(12) United States Patent
Dasgupta et al.

(10) Patent No.: US 10,219,753 B2
(45) Date of Patent: Mar. 5, 2019

(54) HEALTH MONITORING, SURVEILLANCE AND ANOMALY DETECTION

(71) Applicant: ZANSORS LLC, McLean, VA (US)

(72) Inventors: Abhijit Dasgupta, Germantown, MD (US); Ranjit Das, Germantown, MD (US)

(73) Assignee: ZANSORS LLC, McLean, VA (US)

( * ) Notice: Subject to any disclaimer, the term of this patent is extended or adjusted under 35 U.S.C. 154(b) by 0 days.

(21) Appl. No.: 14/212,747

(22) Filed: Mar. 14, 2014

(65) Prior Publication Data

US 2014/0276167 A1    Sep. 18, 2014

Related U.S. Application Data

(60) Provisional application No. 61/788,165, filed on Mar. 15, 2013.

(51) Int. Cl.
| | | |
|---|---|---|
| A61B 5/08 | (2006.01) | |
| A61B 5/00 | (2006.01) | |
| A61B 5/024 | (2006.01) | |
| A61B 5/11 | (2006.01) | |
| A61B 5/145 | (2006.01) | |

(52) U.S. Cl.
CPC .......... *A61B 5/7203* (2013.01); *A61B 5/4818* (2013.01); *A61B 5/024* (2013.01); *A61B 5/02438* (2013.01); *A61B 5/0816* (2013.01); *A61B 5/0826* (2013.01); *A61B 5/1118* (2013.01); *A61B 5/14532* (2013.01); *A61B 5/4806* (2013.01); *A61B 5/4866* (2013.01); *A61B 5/6822* (2013.01); *A61B 5/6833* (2013.01); *A61B 2503/04* (2013.01); *A61B 2505/09* (2013.01)

(58) Field of Classification Search
USPC ....................................................... 600/529
See application file for complete search history.

(56) References Cited

U.S. PATENT DOCUMENTS

| | | | |
|---|---|---|---|
| 4,220,142 A | | 9/1980 | Rosen et al. |
| 5,704,345 A | * | 1/1998 | Berthon-Jones ....... A61B 5/087 128/204.21 |
| 5,797,852 A | | 8/1998 | Karakasoglu et al. |
| 6,290,654 B1 | | 9/2001 | Karakasoglu |
| 6,425,861 B1 | | 7/2002 | Haberland et al. |
| 6,666,830 B1 | | 12/2003 | Lehrman et al. |
| 6,734,802 B2 | | 5/2004 | Halleck et al. |
| 7,141,021 B2 | | 11/2006 | Sullivan et al. |
| 7,297,119 B2 | | 11/2007 | Westbrook et al. |
| 7,371,220 B1 | * | 5/2008 | Koh ..................... A61B 5/0809 600/529 |
| 7,559,903 B2 | | 7/2009 | Moussavi et al. |
| 8,478,418 B2 | | 7/2013 | Fahey |

(Continued)

OTHER PUBLICATIONS

International Search Report and Written Opinon from PCT/US2014/027831 dated Aug. 11, 2015.

(Continued)

*Primary Examiner* — Michael R Bloch
(74) *Attorney, Agent, or Firm* — DLA Piper LLP US

(57) ABSTRACT

A wearable patch and method for automatically monitoring, screening, and/or reporting events related to one or more health conditions (e.g., sleeping or breathing disorders, physical activity, arrhythmias) of a subject.

17 Claims, 7 Drawing Sheets

(56) References Cited

U.S. PATENT DOCUMENTS

| | | | |
|---|---|---|---|
| 2002/0013538 A1 | 1/2002 | Teller | |
| 2002/0193697 A1* | 12/2002 | Cho et al. | 600/529 |
| 2005/0004439 A1* | 1/2005 | Shin et al. | 600/365 |
| 2005/0115561 A1* | 6/2005 | Stahmann et al. | 128/200.24 |
| 2007/0239057 A1* | 10/2007 | Pu et al. | 600/529 |
| 2008/0190430 A1 | 8/2008 | Melker et al. | |
| 2008/0319333 A1* | 12/2008 | Gavish et al. | 600/529 |
| 2009/0105556 A1 | 4/2009 | Fricke et al. | |
| 2010/0204614 A1 | 8/2010 | Lindquist et al. | |
| 2011/0132378 A1 | 6/2011 | Levendowski et al. | |
| 2011/0218409 A1* | 9/2011 | Kugler et al. | 600/301 |
| 2011/0288431 A1 | 11/2011 | Alshaer et al. | |
| 2011/0295083 A1 | 12/2011 | Doelling et al. | |
| 2012/0071741 A1 | 3/2012 | Moussavi et al. | |
| 2012/0238845 A1 | 9/2012 | Yang | |

OTHER PUBLICATIONS

International Preliminary Report on Patentability from PCT/US2014/027831 dated Sep. 24, 2015.

* cited by examiner

HEALTH MONITORING, SURVEILLANCE AND ANOMALY DETECTION

CROSS REFERENCE TO RELATED APPLICATIONS

This application claims priority from U.S. Provisional Application Ser. No. 61/788,165, filed Mar. 15, 2013, the entirety of which is incorporated herein by reference.

FIELD OF THE INVENTION

Embodiments of the invention relate to the wireless monitoring of one or more health and/or wellness conditions of a subject using, for example, a wearable patch designed to automatically monitor, screen, and/or report events related to such conditions (e.g., sleeping, arrhythmias, breathing disorders, metabolic and nutritional status, glucose monitoring, lipid monitoring, type and intensity of physical activity, calorimetry) with on-board embedded processing for anomaly detection.

BACKGROUND

Sleep apnea (SA) is the most common disorder observed in the practice of sleep medicine and is responsible for more mortality and morbidity than any other sleep disorder. SA is characterized by recurrent failures to breathe adequately during sleep (termed apneas or hypopneas) as a result of obstructions in the upper airway.

Nocturnal polysomnography (PSG) is often used for sleep apnea diagnosis. PSG studies are performed in special sleep units and generally involve monitoring several physiological recordings such as electrocardiograms (ECG or EKG), electroencephalograms (EEG), electromyograms (EMG), electrooculograms (EOG), airflow signals, respiratory effort, and oxygen saturation (SaO2) or oximetry. These signals are typically manually analyzed by a sleep specialist to identify every episode of apnea/hypopnea. The number of detected events is divided by the hours of sleep to compute the apnea-hypopnea index (AHI), which is used to assess a subject's sleep apnea severity. PSG studies, however, have drawbacks since they are costly, time-consuming, and require subjects to remain overnight in a medical facility, or other room (e.g., office, hotel room), connected to monitoring equipment by a multitude of wires. Current PSG sleep studies monitor motion/movement by using video cameras and sleep technicians manually observing movements after the sleep study. Some sleep studies use actigraphy watches that cost $1,000, with $400 software licenses.

The last few years have seen increased demand for better breathing/sleep diagnostics. There has been more focus on home breathing/sleep monitoring techniques. These techniques monitor the subject's air flow, EKG and pulse oximetry. As such, these techniques require relatively expensive equipment (e.g., $400 to $1,000) that is very bulky and requires many wires to be connected between the equipment worn by the test subject (e.g., headgear, Holter monitor) and the diagnostic equipment. As can be appreciated, the bulkiness of the equipment worn by the subject and the need to maintain the multitude of wired connections throughout the study makes the study very uncomfortable for the test subject. Should the subject desire to get out of bed during the study (e.g., a trip to the bathroom, a desire to walk around, etc.), all of the wires would need to disconnected and then reconnected to continue the study. Moreover, the study is prone to errors or may even need to be re-done should one or more wires become disconnected during the study. All of these scenarios are undesirable for both the subject and the medical facility.

Patient surveillance and telemedicine have an increasing importance in providing appropriate and timely healthcare services. Current patient reporting outcomes require a patient to complete surveys/questionnaires using paper-based methods inside a clinic even though remote mobile technologies allow for simpler data collection using digital tools and mobile devices. As patients are discharged from a medical facility to their home, important patient outcomes may be missed due to lack of reporting modalities and surveillance and result in costly hospitalizations. In addition, the last few years have seen the introduction of stylish wrist-worn monitors that count the number of steps even though cheap consumer pocket pedometers have been around for years. These stylish wrist-based pedometers are mere novelties that do not offer real utility in monitoring either health or wellness measures. The potential utility of such devices is also not maximized since on-board, embedded algorithms can be costly and require significant battery and memory, which are limited given the stylish form factor of these devices.

Accordingly, there is a need and desire for a better monitoring technique that overcomes the above-noted limitations associated with PSG, Holter monitors and home monitoring techniques.

SUMMARY

Embodiments of the invention relate to the wireless monitoring of one or more health and/or wellness conditions of a subject using, for example, a wearable patch designed to automatically monitor, screen, and/or report events related to such conditions (e.g., sleeping, arrhythmias, breathing disorders, metabolic and nutritional status, glucose monitoring, lipid monitoring, type and intensity of physical activity, calorimetry), with on-board embedded algorithms for anomaly detection. In addition, a technological ecosystem comprising mobile devices, sensor-based patches and cloud-based computing and data storage along with novel processing/algorithms for anomaly detection allows timely monitoring and surveillance of patients using both objective (sensor) and subjective (patient reported outcomes via a mobile application) data, delivered in consumable form to caregivers and health practitioners (via a health and wellness dashboard, for example). In addition, novel processing in a cloud computing database provides health surveillance from objective data (e.g. sensor) and self-report data (e.g. mobile application) that can be visualized on a health dashboard.

Embodiments disclosed herein provide a method of wirelessly monitoring a condition of a subject. The method comprising wirelessly capturing, at a processor, a first signal indicative of the condition over a first period of time; removing, at the processor, noise from the captured first signal to create a second signal indicative of the condition; computing, at the processor, a plurality of moving averages of the second signal using a window defining a second period of time; and determining if there has been an event associated with the condition within any of the windows.

DETAILED DESCRIPTION

In the following detailed description, a plurality of specific details, such as types of materials and dimensions, are set forth in order to provide a thorough understanding of the preferred embodiments discussed below. The details discussed in connection with the preferred embodiments should not be understood to limit the claimed invention. Furthermore, for ease of understanding, certain method steps are delineated as separate steps; however, these steps should not be construed as necessarily distinct nor order dependent in their performance.

Figure 1:
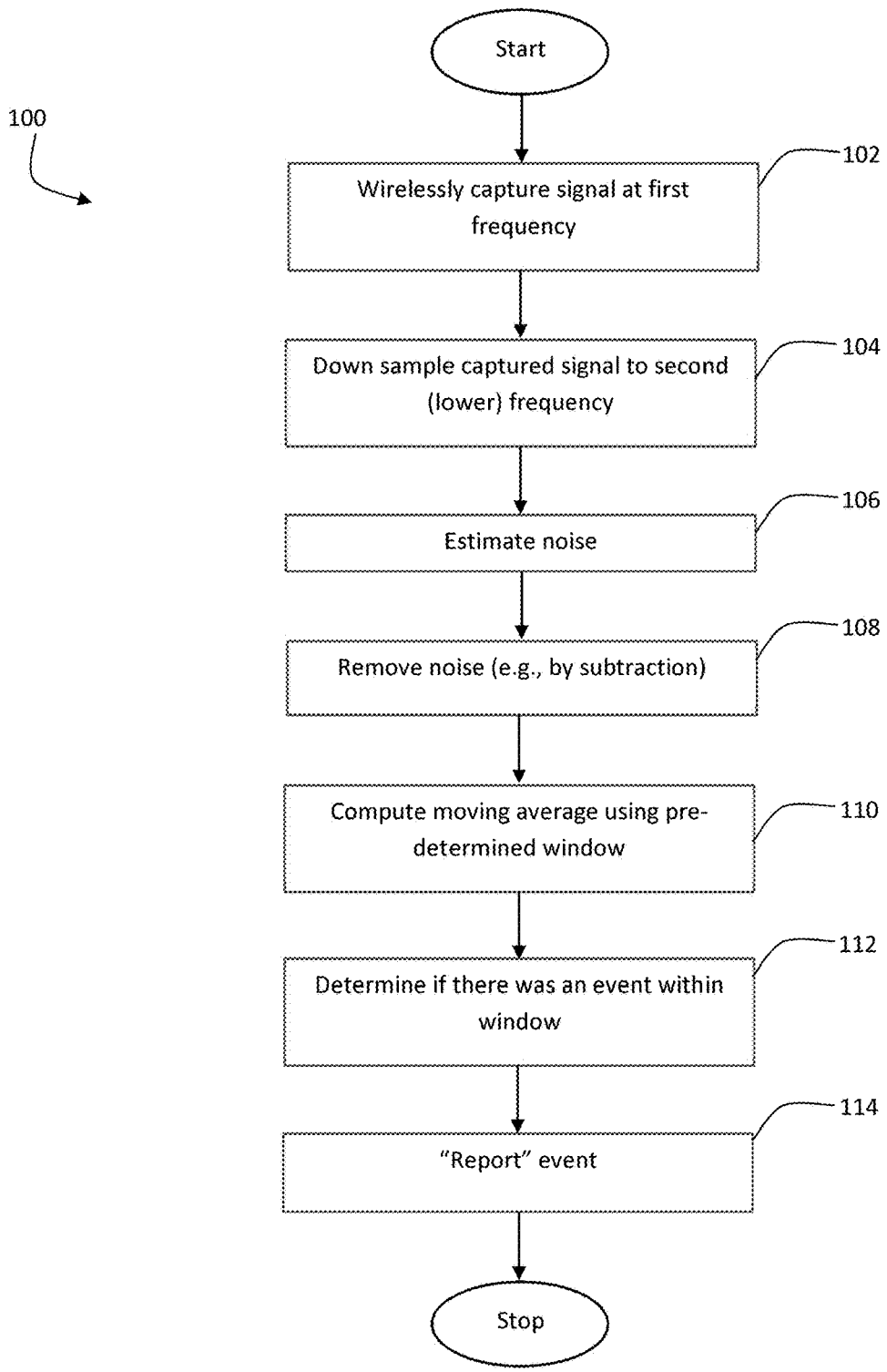
FIG. 1 illustrates an example wireless monitoring method in accordance with a disclosed embodiment.

FIG. 1 illustrates an example wireless monitoring method 100 in accordance with a disclosed embodiment. In a desired embodiment, the method 100 is implemented using a wireless wearable device such as e.g., the novel patches 300, 400, 500, 600 discussed below with reference to FIGS. 3-9. In one embodiment, the method 100 is implemented as software instructions that are stored on the patches 300, 400, 500, 600 and executed by a processor or other controller included on the patches 300, 400, 500, 600. In other embodiments, the method 100 is implemented as software instructions provided in part on the patches 300, 400, 500, 600 and in part on an application program (e.g., smartphone application) remote from the patches as is discussed below in more detail.

The method 100 is explained with reference to monitoring conditions related to sleep apnea; it should be appreciated, however, that the method 100 can be used to monitor and diagnose other medical conditions such as, but not limited to, asthma, pneumonia, chronic obstructive pulmonary disease (COPD), congestive heart failure, arrhythmias, restless leg syndrome, seizures, falls, metabolic/nutritional levels (e.g. glucose and lipid monitoring) and sudden infant death syndrome (SIDS). Several "wellness" conditions can be monitored besides health conditions: physical activity monitoring (intensity and type, calorie expenditure, and sedentary vs. activity analysis), baby monitoring, sexual activity from breaths, Internet of Things applications requiring sounds, breathing effort from sports and entertainment, sentiment analysis from an input using mobile applications, and linking subjective information from a mobile application with objective data from method 100 to provide a holistic picture of health, wellness and activity of the individual. As will become apparent from the following description, the method 100 and patches 300, 400, 500, 600 disclosed herein will wirelessly record sounds (via e.g., a microphone) and movements (via e.g., an accelerometer) that can be immediately processed and reported by one or multiple mechanisms, without the need for manual/visual evaluation by medical personnel as is currently required with today's sleep studies. The assignee of the present application has other sensors that can be placed on a patch with embedded processing such as for example micro-electrode arrays that capture electrical and neural signals for anomaly detection, integrated multi-sensors for physiological monitoring (e.g., pressure, humidity, inertia, temperature), and microfluidic patches that measure biofluid levels (e.g., glucose, metabolic analytes, etc.).

The method 100 begins at step 102 where a signal representative of the subject's breathing (hereinafter referred to as a "breathing signal") is wirelessly captured using a first sampling frequency. In one embodiment, the breathing signal is captured by a microphone or other acoustic sensor included on a patch (e.g., 300, 400, 500, 600) worn by the subject. In one embodiment, the sampling frequency is 44.1 kHz, which is often used with digital audio recording equipment. It should be appreciated, however, that the 44.1 kHz frequency is just one example frequency that could be used and that the embodiments disclosed herein are not limited solely to the 44.1 kHz frequency. All that is required is for the breathing signal to be continuously captured using a rate fast enough to properly sample the subject's breathing. In one embodiment, as applied to health and wellness monitoring generally, the frequency at which sound will be captured can be greatly reduced, enabling lower requirements for memory and power, since most biological processes occur at frequencies closer to 1-2 Hz, if not lower. This reduction can also be applied to other embodiments using other sensors, since biological processes generally occur at low frequencies, of the order of seconds, minutes, hours, days or weeks between detectable events.

It should be appreciated that sounds caused by the subject's breathing must be identified in the background of other rhythmic or incidental sounds that can be recorded. The embodiments disclosed herein have been calibrated to filter extraneous and irrelevant sounds. Data was collected from various subjects and analyzed. Statistical analysis, frequency analysis, signal processing and power spectrum of various breathing, heartbeat and other sounds were used to develop digital profiles, which characterize the respiratory rate (e.g., normal or abnormal inspiration/expiration), breathing patterns (e.g., rhythmic) and quality of breathing (e.g., normal, shallow) that can be used to hone in on the breathing signal at step 102. These profiles can be used to distinguish between mild, moderate and severe sleep apnea. For example, a microphone sensor might capture the pulse in addition to breathing sounds. The profiles for these two sounds will be quite different, since the pulse beats on the order of 60-100 beats per minute, while breathing will typically be below 20 breaths per minute. Frequency analysis can distinguish the two profiles and filter out the higher frequency profile. Anomalies that disrupt the regular nature of the profile can be used to assess frequency and severity of abnormalities like apneic events.

The disclosed embodiments and their embedded processing/algorithms can develop digital profiles of different sounds, distinguish them, filter some profiles as necessary, and identify anomalous events that disrupt the normal profile specific to the user that is determined through monitoring the user over an appropriate period of time. The processing also takes into account the possibility of low available resources such as battery and available memory, as well as data transmission requirements to still achieve the stated purpose. The embodiments utilize a carefully selected bill of materials/components, designed electrical schematics, and designed embedded software architecture that creates a wireless system while also incorporating an algorithm/processing that can manage battery and memory space, and provide wireless transmissions. The disclosed embodiments successfully implement and use a microphone capable of collecting information at 20 Hz-300 Hz. By contrast, the typical MEMS microphones used in cell phones that need 300-3000 Hz response would suffer from poor low frequency response. The disclosed embodiments also overcome challenges faced with the positioning of the microphone that has to be pointed at the subject or away from the subject. Microphones mounted close to the sound source can suffer from excess low frequency response and distortion. This is due to the sound pressure arriving at the same time as the entire structure is vibrating from the same sound. This causes signal cancelling and enhancement that varies with frequency.

Figure 2A:
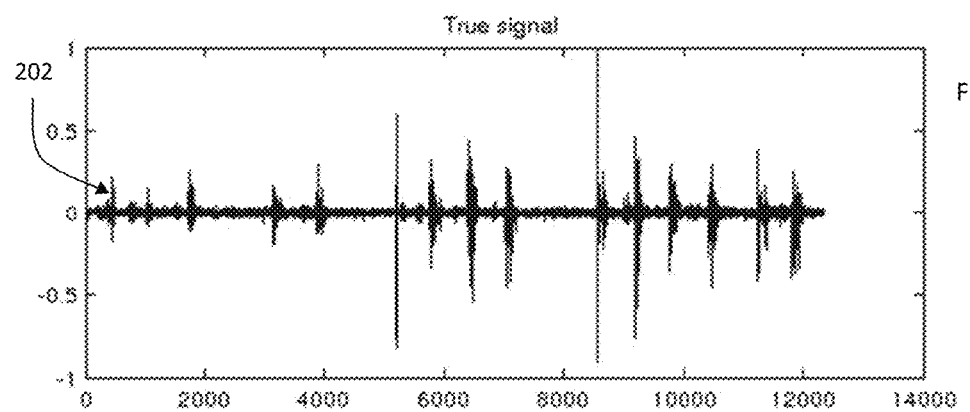
FIGS. 2a-2c are graphs illustrating example results of the FIG. 1 method.

At step 104, the captured breathing signal is down-sampled to a second, much lower frequency. In one embodiment, the signal is down-sampled to 100 Hz. It should be appreciated, however, that the 100 Hz frequency is just one example frequency that could be used and that the embodiments disclosed herein are not limited solely to the 100 Hz frequency. This level can be adjusted based on the particular profile that is being targeted and the resources available to capture the data. This reduces the amount of data needed to be analyzed in subsequent steps. FIG. 2a illustrates a graph comprising an example captured signal 202 that has been down sampled to 100 Hz.

It should be appreciated that noise may be present during the monitoring of the subject and that this noise could impact the signal being captured. For example, there could be background noise, ambient noise from air in the room, and/or electrical noise that could be picked up when capturing the breathing signal. It should be appreciated that the target signal desired to be captured needs to be of higher intensity than the ambient noise captured either as part of background noise or as an intrinsic artifact generated by the sensor. Accordingly, at step 106, the method 100 estimates the amount of noise present in the captured breathing signal. In one embodiment, the noise is estimated by filtering out portions of the signal with intensity less than twice the standard deviation of the distribution of signal intensity captured over a period of time. In one embodiment, the time period is ten seconds, but it should be appreciated that how the noise is estimated should not limit the embodiments disclosed herein. All that is required is that the method 100 include some processing to estimate low intensity ambient and artifactual noise that then can be removed from the captured signal in step 108. In one embodiment, the estimated noise from step 106 is simply subtracted from the down-sampled breathing signal achieved at step 104. It should be appreciated that other noise removal procedures could be used at step 108.

Figure 2B:
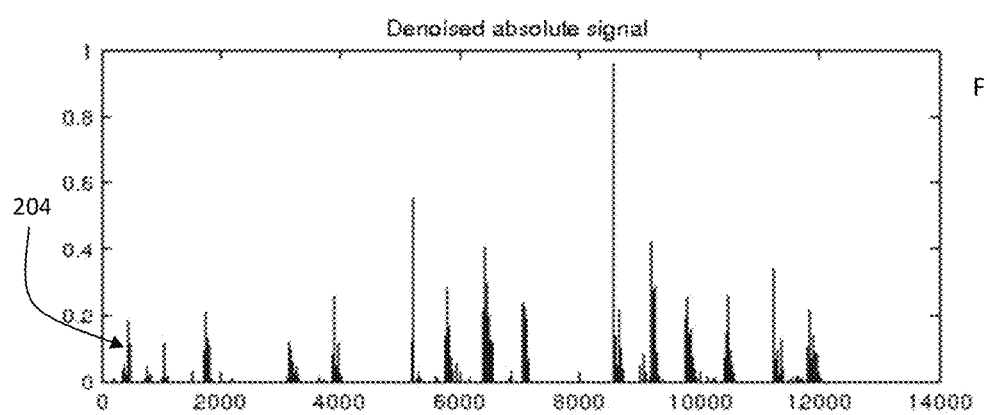

FIG. 2b illustrates a graph comprising an example "denoised" breathing signal 204 resulting from step 108. That is, the captured breathing signal was measured over e.g., a period of ten seconds to determine signal variations and baseline noise on the absolute intensities. A standard deviation was then determined and used to filter low intensity "buzz" from the breathing signal. This way, peaks of the breathing signal become evident and can be used for evaluation purposes (as shown in FIG. 2b). Anomalous events like apneic events are then determined algorithmically. In one embodiment, in order to determine anomalous breathing stoppage, moving averages over a pre-determined temporal window are computed on the digital signal intensities, as shown in step 110. In one embodiment, a ten second window is used as it corresponds to an apneic event (i.e., a sleep apnea event is ten or more seconds without breathing). In embodiments used to diagnose other breathing anomalies, the window could be greater or less than ten seconds, or alternative algorithms can be used, depending on the nature of the anomaly that is being targeted. It should be appreciated that different alternative algorithms are used to identify different anomalous events based on the signal being targeted and the nature of the anomalies to be detected.

Figure 2C:
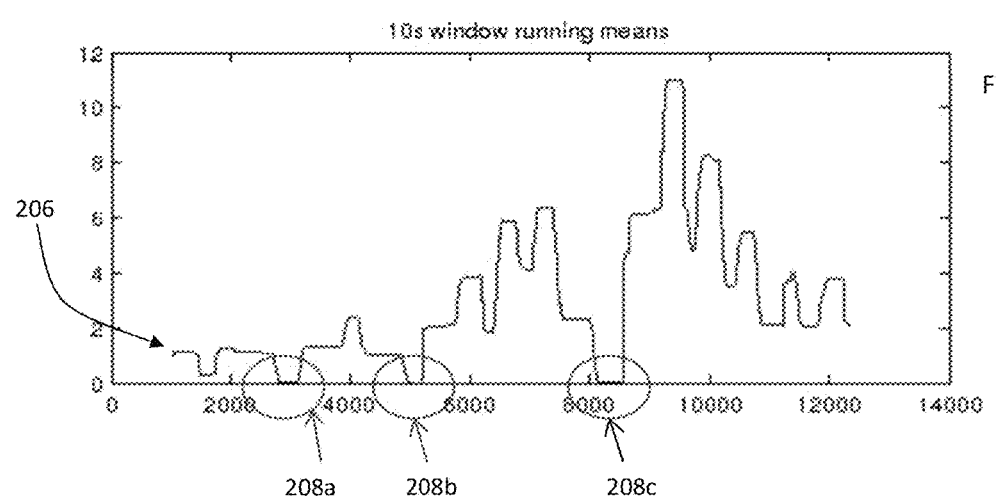

FIG. 2c is a graph illustrating a signal 206 representing the ten second moving average of the denoised signal 204 illustrated in FIG. 2b. The method 100 uses this moving average signal 206 to determine if there have been any events within a ten second window (step 112). For example, an event is detected any time the moving average signal 206 has a value of zero. In the example illustrated in FIG. 2c, there are three events 208a, 208b, 208c detected in this recording because the signal 206 is zero at those points. The method 100 uses a unique counter (as part of step 112) to keep track of these detected events 208a, 208b, 208c. The method 100 continues by "reporting" the events at step 114. Reporting of the events can occur in different ways. In one embodiment, as is discussed below in more detail, the device worn by the subject can include status LEDs to visually display the level of apnea (e.g., mild, moderate, severe) based on a count of the number of apnea events like events 208a, 208b, 208c detected over a period of time, typically overnight. In another embodiment, the number of events can be transmitted from the device worn by the subject so that the information can be processed by a computer, cloud computing infrastructure or smartphone application in communication with the device. Moreover, the event information (and time of the events) can be stored in a memory on and/or off the device worn by the subject for subsequent evaluation.

Thus, as can be appreciated, the method 100 hones in on specified windows of time and determines if an event (e.g., no breathing) occurred during the window. The number of events can then be analyzed to determine the severity of the subject's sleep apnea or other breathing condition without the need for expensive and/or bulky equipment and without the need of manual evaluation by medical personnel. As can be appreciated, the method 100 only stores limited amount of data (e.g., events and time of the events) and thus, has very low memory and computational requirements. Thus, home monitoring and patient surveillance is enhanced with this system.

In one embodiment, the patch (e.g., 300, 400, 500, 600) will include a motion sensor in the form of an accelerometer. The accelerometer measures the rate at which motion changes over time (i.e., acceleration) over three axes. In one embodiment, the motion sensor will be used to detect sudden movements that are typically associated with suddenly waking up, period limb movement, or suddenly gasping for breath. In one embodiment, this data is linked to the sound data to establish particular sleep events such as e.g., apneic events.

Figure 3:
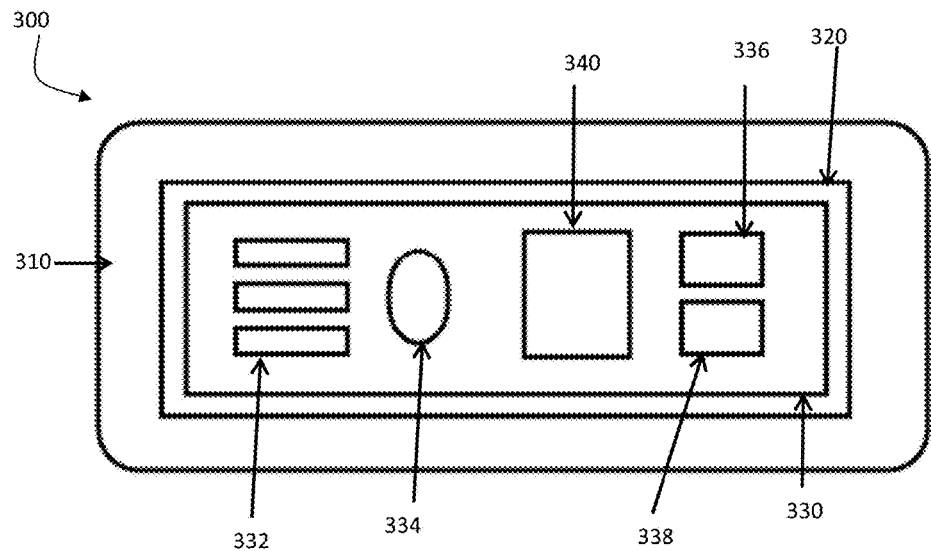
FIGS. 3 and 4 illustrate a wireless monitoring device according to a first example embodiment disclosed herein.
Figure 4:
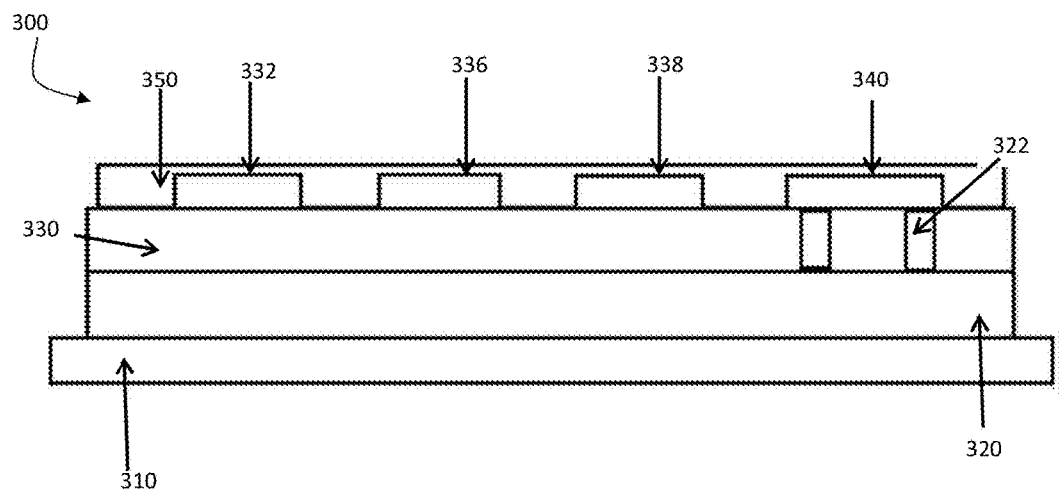

As mentioned above, in one embodiment, the method 100 is implemented as software instructions that are stored on a patch worn by the subject and executed by a processor or other controller included on the patch. FIGS. 3 and 4 illustrate one example patch 300 that may be used to implement the method 100 discussed above. The lowest level of the patch 300 is an adhesive layer 310 that has one side that will be applied to a subject and a second side for supporting the other layers of the patch 300. In one embodiment, the adhesive layer 310 comprises white polyethylene foam such as e.g., 1/16", 4# cross linked polyethylene foam that is coated with an adhesive such as e.g., an aggressive medical grade pressure-sensitive adhesive (e.g., MA-46 acrylic medical grade adhesive). Although not shown, the adhesive side may be protected by a liner or release paper such as e.g., a siliconized polycoated release paper (e.g., 84# siliconized polycoated Kraft release paper). It should be appreciated that the embodiments are not limited to the type of substrate, adhesive or liner (if used) discussed herein and that any suitable substrate, adhesive or liner may be used to form the patch 300.

In the illustrated embodiment, a power source 320 is positioned on, over or within the adhesive layer 310. In one embodiment, the power source 320 is a thin film battery by Cymbet Corp. or Infinite Power Solutions and alternatively one can use Panasonic BR3032 3V Lithium Coin battery. A flexible printed circuit board (PCB) 330 is positioned on or over the power source 320. The flexible printed circuit board 330 may comprise one or more layers and also comprises a plurality of electronic components and interconnections that are used to implement the method 100 discussed above. The illustrated components include a microcontroller 340, an acoustic sensor 336 (e.g., microphone), a movement sensor 338 (e.g., accelerometer), a memory device 334, and a plurality of LEDs 332. Other active (e.g., diodes, LEDs) or passive (e.g., capacitors, resistors) electronic components, mechanical components (e.g., on/off switch) and/or communication components (e.g., RS-232 or JTAG ports) can be included in the PCB 330 if desired. Example of such additional components include, but are not limited to TDK C1005X5R0J474K or Yageo CC0402JRNPO9BN120 capacitors, and Panasonic ECG ERJ-2GE0R00X resistors. Power to the electronic components of the PCB 330 is received through vias 322 connected to the power source 320. Although not shown, the components in the PCB 330 are interconnected by interconnects formed in or attached to the PCB 330 or other layers in the patch 300. Examples of suitable interconnects include e.g., embedded fine copper wire, etched silver plating, conductive polymers or flexible circuit boards; all of these interconnections are very flexible and readily available.

In one embodiment, the top portion of the patch 300 is encapsulated by a protective coating 350 to provide protection (e.g., water-proofing) for the components and other layers in the patch 300. One or more notches (not shown) may be provided through the coating 350 to reveal all or part of the acoustic sensor 336. In one embodiment, the coating 350 is see-through at least over the portion of the patching containing the LEDs 332 so that the LEDs 332 are visible. Additionally or alternatively, the coating 350 can contain a design and/or colors rendering the patch 300 esthetically pleasing to the subject and others.

As can be appreciated, the microcontroller 340 will implement all of the steps of method 100. The memory 334 can include calibration tables, software instructions and/or other data needed to implement the method 100 under control of the microcontroller 340. The microcontroller 340 will input signals received by the acoustic and/or movement sensors 336, 338, perform the processing described above with reference to FIG. 1 and "report" detected events. In the illustrated embodiment, the patch 300 will "report" events via the LEDs 332, which can have different colors for different possible health/event statuses. For example, the LEDs 332 can have one color indicative of normal sleep/breathing (i.e., no apnea), one color for mild apnea, one color for moderate apnea and/or one color for severe apnea, or any combination of thereof. Moreover, one of the LEDs 332 may be used as a power indicator. As noted above, detected events and other information (e.g., time of the events) can be stored in the memory 334 for subsequent downloading (via a communication or JTAG port) and processing by an external device such as e.g., a computer, cloud computing database based on unstructured database software like MongoDB, real-time health dashboard built with Python data stacks, HTML5 web pages, and javascript graphic libraries.

Figure 5:
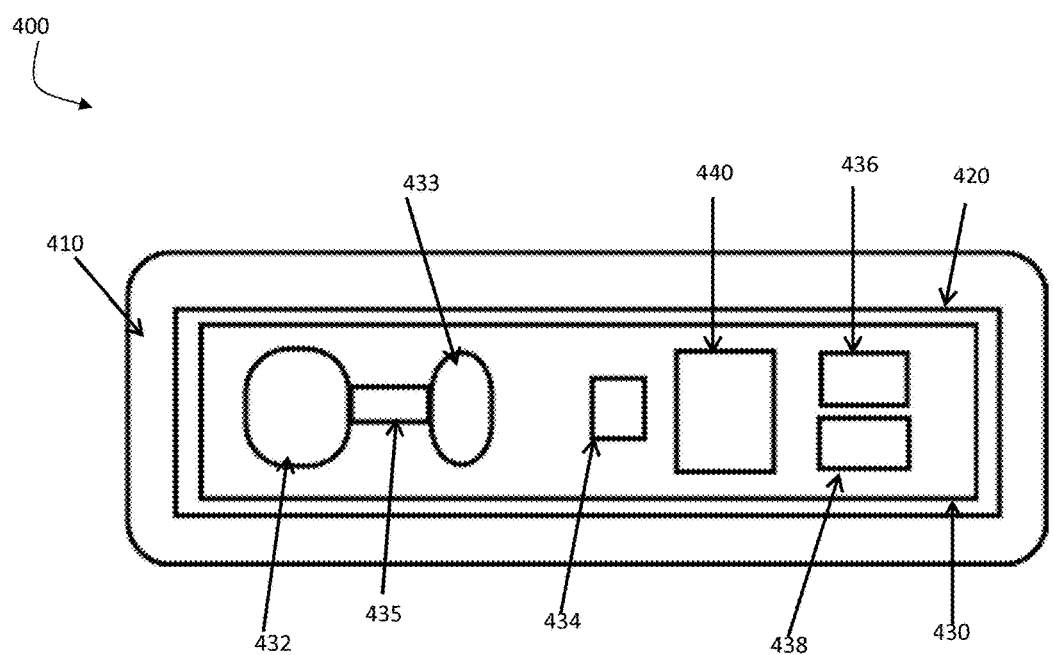
FIG. 5 illustrates a wireless monitoring device according to a second example embodiment disclosed herein.

FIG. 5 illustrates another example patch 400 that may be used to implement the method 100 discussed above. The lowest level of the patch 400 is an adhesive layer 410 that has one side that will be applied to a subject and a second side for supporting the other layers of the patch 400. The adhesive layer 410 can comprise the same materials as the materials discussed above with respect to patch 300. It should be appreciated, however, that the embodiments are not limited to the type of substrate, adhesive or liner (if used) discussed herein and that any suitable substrate, adhesive or liner may be used to form the patch 400.

In the illustrated embodiment, a power source 420 is positioned on, over or within the adhesive layer 410. In one embodiment, the power source 420 is a thin film battery such as the one discussed above for patch 300. A flexible printed circuit board (PCB) 430 is positioned on or over the power source 420. The flexible printed circuit board 430 may comprise one or more layers and also comprises a plurality of electronic components and interconnections that are used to implement the method 100 discussed above. The illustrated components include a microcontroller 440, an acoustic sensor 436 (e.g., microphone), a movement sensor 438 (e.g., accelerometer), a memory device 434, communication integrated circuit (IC) 433 and an antenna 432 connected to the communication IC 433 by a suitable interconnect 435. In one embodiment, the communication IC 433 implements wireless Bluetooth communications (e.g., Texas Instrument CC2540 2.4 GHz Bluetooth Low Energy System-on-Chip). It should be appreciated, however, that any type of wireless communications can be implemented and, as such, the communication IC 433 is not to be limited solely to an integrated circuit capable of performing Bluetooth communication. In addition, it should be appreciated that other active (e.g., diodes, LEDs) or passive (e.g., capacitors, resistors) electronic components, mechanical components (e.g., on/off switch) and/or communication components (e.g., RS-232 or JTAG ports) can be included in the PCB 430 if desired. Power to the electronic components of the PCB 430 is received through vias (not shown) connected to the power source 420 in a manner similar to the manner illustrated for patch 300 (e.g., FIG. 4). Although not shown, the components in the PCB 430 are interconnected by interconnects formed in or attached to the PCB 430 or other layers in the patch 400. Examples of suitable interconnects include e.g., embedded fine copper wire, etched silver plating, conductive polymers or flexible circuit boards; all of these interconnections are very flexible and readily available.

In one embodiment, the top portion of the patch 400 is encapsulated by a protective coating similar to the coating discussed above with respect to patch 300. One or more notches may be provided through the coating to reveal all or part of the acoustic sensor 436 and/or antenna 432. Unlike the coating used for patch 300, the coating used for patch 400 would not need to be see through unless LEDs or other visual indicators are contained on the PCB 430. Additionally or alternatively, the coating can contain a design and/or colors rendering the patch 400 esthetically pleasing to the subject and others.

In one embodiment, the microcontroller 440 will implement all of the steps of method 100. The memory 434 can include calibration tables, software instructions and/or other data needed to implement the method 100 under control of the microcontroller 440. The microcontroller 440 will input signals received by the acoustic and/or movement sensors 436, 438, perform the processing described above with reference to FIG. 1 and "report" detected events. In the illustrated embodiment, the patch 400 will "report" events by transmitting event data (e.g., detected events, time of detected events) to an external device (e.g., a computer, smartphone). The external device can then display, print and/or record the event data as desired. As noted above, detected events and other information (e.g., time of the events) can be stored in the memory 434 for subsequent downloading (via a communication or JTAG port) and processing by an external device such as e.g., a computer.

Figure 6:
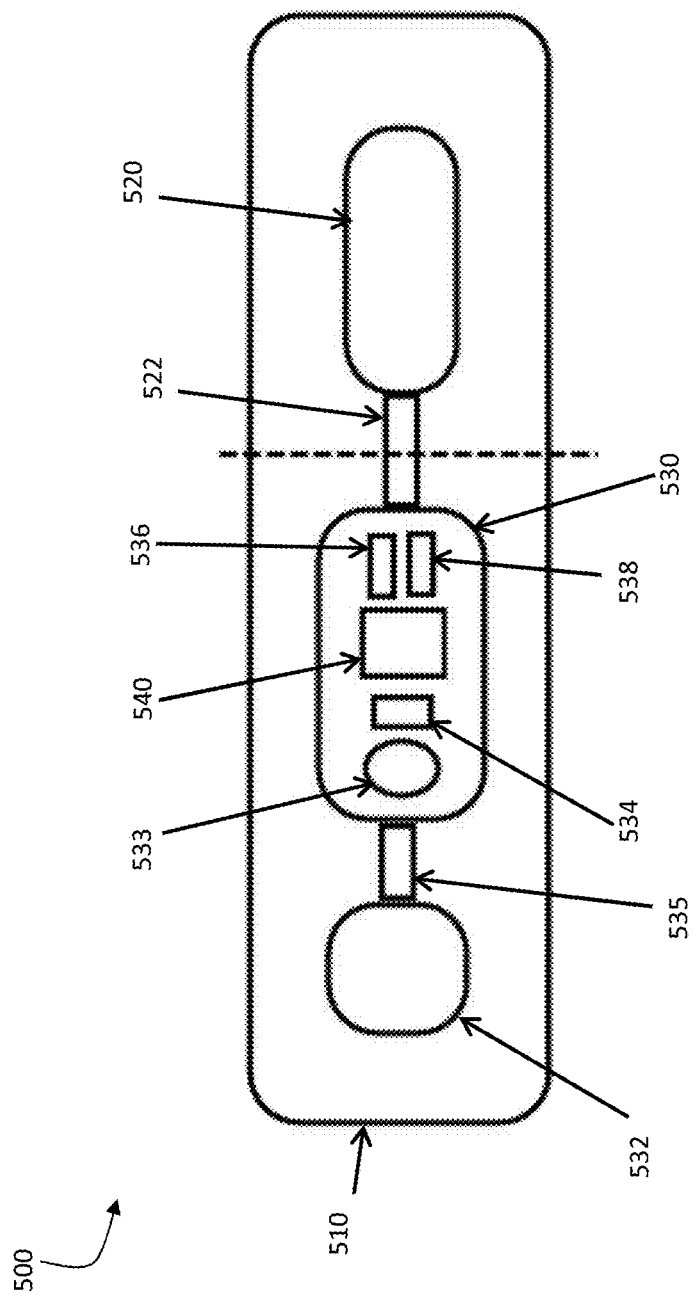
FIG. 6 illustrates a wireless monitoring device according to a third example embodiment disclosed herein.

FIG. 6 illustrates an example of a patch 500 similar to patch 400 of FIG. 5. That is, patch 500 may be used to implement the method 100 discussed above. The lowest level of the patch 500 is an adhesive layer 510 that has one side that will be applied to a subject and a second side for supporting the other layers of the patch 500. The adhesive layer 510 can comprise the same materials as the materials discussed above with respect to patch 300. It should be appreciated, however, that the embodiments are not limited to the type of substrate, adhesive or liner (if used) discussed herein and that any suitable substrate, adhesive or liner may be used to form the patch 500.

In the illustrated embodiment, however, a power source 520 is positioned on, over or within the adhesive layer 510 on the same level as the flexible printed circuit board (PCB) 530 and antenna 532. In one embodiment, the portion of the adhesive layer 510 comprising the power source 520 may be folded underneath the portion of the layer 51 comprising the PCB 530 and antenna. In this configuration, the adhesive would be applied to the portion of the folded layer 510 that would contact the subject's skin. This would allow the two portions to be separated (see dashed line) after the patch has been used (discussed in detail below). The power source 520 is connected to the PCB 530 using a suitable interconnect or via 522. In one embodiment, the power source 520 is a thin film battery such as the one discussed above for patch 500. The flexible printed circuit board 530 may comprise one or more layers and also comprises a plurality of electronic components and interconnections that are used to implement the method 100 discussed above. The illustrated components include a microcontroller 540, an acoustic sensor 536 (e.g., microphone), a movement sensor 538 (e.g., accelerometer), a memory device 534 and a communication integrated circuit (IC) 533 connected to the antenna 532 by a suitable interconnect 535. In one embodiment, the communication IC 533 implements wireless Bluetooth communications. It should be appreciated, however, that any type of wireless communications can be implemented and, as such, the communication IC 533 is not to be limited solely to an integrated circuit capable of performing Bluetooth communication. In addition, it should be appreciated that other active (e.g., diodes, LEDs) or passive (e.g., capacitors, resistors) electronic components, mechanical components (e.g., on/off switch) and/or communication components (e.g., RS-232 or JTAG ports) can be included in the PCB 530 if desired. Although not shown, the components in the PCB 530 are interconnected by interconnects formed in or attached to the PCB 530 or other layers in the patch 500. Examples of suitable interconnects include e.g., embedded fine copper wire, etched silver plating, conductive polymers or flexible circuit boards; all of these interconnections are very flexible and readably available.

In one embodiment, the top portion of the patch 500 is encapsulated by a protective coating similar to the coating discussed above with respect to patch 300. One or more notches may be provided through the coating to reveal all or part of the acoustic sensor 536 and/or antenna 532. Unlike the coating used for patch 300, the coating used for patch 500 would not need to be see through unless LEDs or other visual indicators are contained on the PCB 530. Additionally or alternatively, the coating can contain a design and/or colors rendering the patch 500 esthetically pleasing to the subject and others.

In one embodiment, the microcontroller 540 will implement all of the steps of method 100 in the same manner as microcontroller 440 of patch 400. Likewise, the memory 534 can include calibration tables, software instructions and/or other data needed to implement the method 100 under control of the microcontroller 540. The microcontroller 540 will input signals received by the acoustic and/or movement sensors 536, 538, perform the processing described above with reference to FIG. 1 and "report" detected events. In the illustrated embodiment, the patch 500 will "report" events by transmitting event data (e.g., detected events, time of detected events) to an external device (e.g., a computer, smartphone). The external device can then display, print and/or record the event data as desired. As noted above, detected events and other information (e.g., time of the events) can be stored in the memory 534 for subsequent downloading (via a communication or JTAG port) and processing by an external device such as e.g., a computer.

Figure 7:
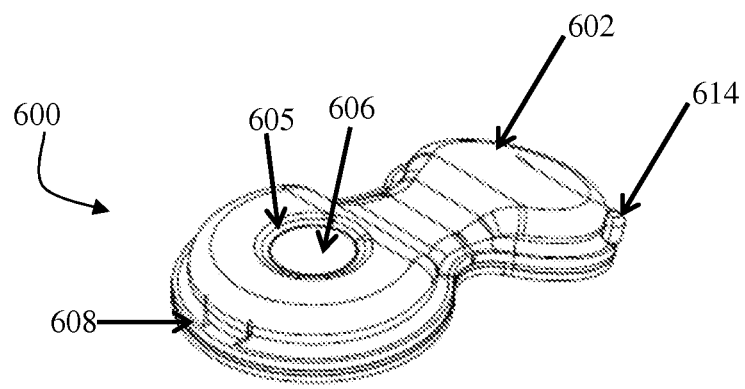
FIGS. 7-9 illustrate a wireless monitoring device according to a fourth example embodiment disclosed herein.
Figure 8:
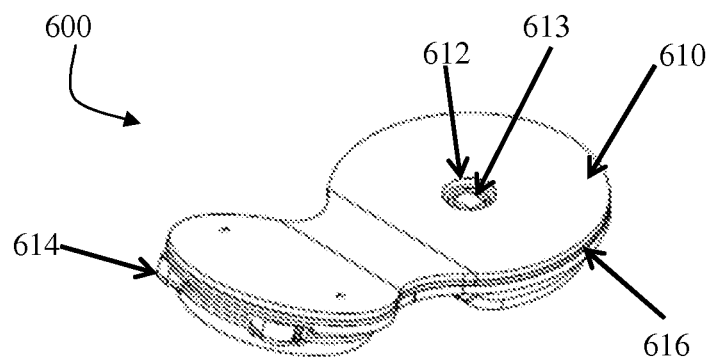
Figure 9:
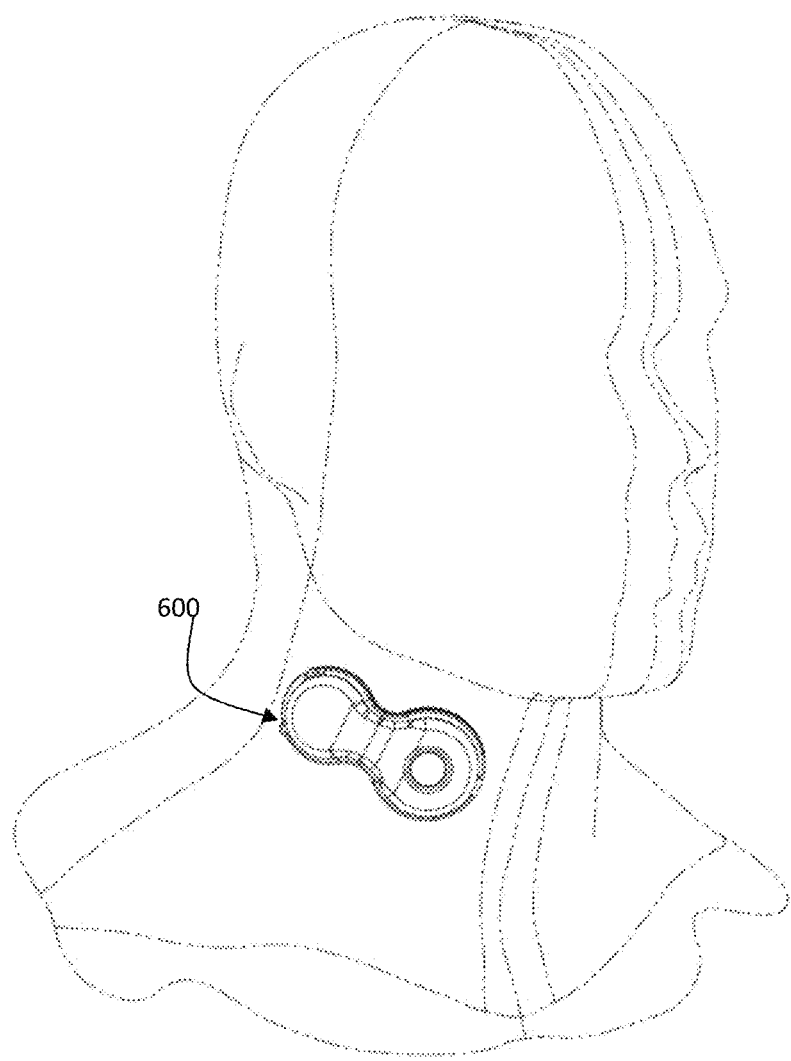

FIGS. 7-9 illustrate a wireless monitoring patch 600 according to a fourth example embodiment disclosed herein. Internally, the patch 600 can include any of the electronic components and circuitry identified above and will be able to execute the method 100 disclosed herein. In the example embodiment, the patch 600 includes a durable foam exterior cover 602 that has a hole 605 exposing a component 606 connected to the internal circuitry of the patch 600. In the illustrated embodiment, the component 606 is a button having a multicolor backlight that can be used e.g., as an on/off button and the multi-colored LEDs discussed above.

The example cover 602 also includes a port 608 for an external connection (such as e.g., a USB device) and an access tray 614 for a battery. The bottom of the patch 600 includes an adhesive pad 610 and a semi-flexible frame 616 between the pad 610 and cover 602 that supports the internal components/circuitry of the patch 600. In one embodiment, the cover 602, internal components, frame 616 and pad 610 are bonded together. In the illustrated example, the pad 610 and frame 616 contain a hole 612 that exposes an internal component 613 of the patch 600. In the illustrated embodiment, the component 613 is a microphone.

As can be appreciated, regardless of the patch used to implement the method 100, it is desirable to save and re-use as many components as possible. That is, because the patches 300, 400, 500, 600 contain different layers, it is possible to configure the patches 300, 400, 500, 600 to reuse some or all of the most expensive equipment by separating the desired component/layer from a disposable adhesive layer and applying the component/layer on a new and unused adhesive layer. Example configurations include: (1) having a disposable adhesive layer with a battery and the antenna, with other reusable layers comprising the remaining electronics (e.g., PCB, microcontroller, memory, sensors, communication IC, LEDs, etc.); (2) having a disposable adhesive layer with a battery, with other reusable layers comprising the remaining electronics (e.g., PCB, microcontroller, memory, sensors, communication IC, antenna, LEDs, etc.); or (3) having the entire patch with electronics and power source as being disposable.

In one embodiment, the patch 300, 400, 500, 600 is placed on the subject's throat (as shown in FIG. 9), which provides both a comfortable location as well as a strong signal from breathing. Other possible locations include the subject's cheek, nose or chest. The location on the throat not only allows capture of breathing sounds, but it can capture other bio-signals like the acoustic sounds from blood vessels. The disclosed algorithm's efficient processing and calculations allows a small sized device that is wireless, but more importantly, that can then be attached to any part of the body including the chest or limbs (i.e., not just on the neck or nose). Thus, the disclosed processing can measure periodic limb movement physical rehabilitation as a health condition or can monitor new levels of activity for physical activity.

The disclosed algorithm/processing can be used for health monitoring within a sensor device to collect objective data or the algorithm/processing can be used as a health surveillance tool that relies on e.g., a smartphone application, cloud computing database, and/or health dashboard. In a health surveillance mode, the disclosed algorithm/processing will aggregate streams of data from the sensor and application and the algorithm residing in the cloud database will conduct real-time calculations based on pre-programmed rules for outlier activity or patterns. If the rule/algorithm embedded in the device or cloud database detects an outlier or anomaly pattern, then a digital visualization will be created on a health dashboard so that a physician or nurse can identify the patient who may need more assistance. In other words, the algorithm generates a red-yellow-green dashboard. This data visualization is not limited to the physician or nurse but can also be rendered on a consumer's own device or screen. In one embodiment, the smartphone application will capture notes input by the user that will be analyzed using natural language processing techniques and linked to the sensor data to corroborate and validate the user's perception and experience, as well as provide information to caregivers and the user about the subjective and perceptual effect of any anomalies on the user.

The method 100 and patches 300, 400, 500, 600 disclosed herein provide numerous advantages over existing monitoring techniques. For example, the disclosed monitoring can be performed in an inexpensive manner with respect to the components used. This is partially achieved by processing and storing small amounts of data (e.g., events, time of events), allowing the use of smaller memories and less computations, as opposed to storing and processing an entire evening's worth of information from a multitude of sensors. The components used and the processing performed by method 100 allow for the use of a small power source, which can be disposed of and replaced by another power source for subsequent uses. As such, all of the patches 300, 400, 500, 600 will be easily affordable by the subject. Moreover, as discussed above, the small size of the patch 300, 400, 500, 600 and the lack of wires makes the disclosed embodiments much more comfortable to use and is less likely to experience errors (such as those associated with disconnected wires in current techniques). Another benefit is that the algorithm unifies both hardware and software solutions to create a seamless, interoperable technological ecosystem. The interoperability is a significant unmet need in the health information technology space especially in home-based and remote monitoring settings The foregoing examples are provided merely for the purpose of explanation and are in no way to be construed as limiting. While reference to various embodiments is made, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and uses, such as are within the scope of the appended claims.

Additionally, the purpose of the Abstract is to enable the patent office and the public generally, and especially the scientists, engineers and practitioners in the art who are not familiar with patent or legal terms or phraseology, to determine quickly from a cursory inspection the nature of the technical disclosure of the application. The Abstract is not intended to be limiting as to the scope of the present inventions in any way.

What is claimed is:

1. A method of wirelessly monitoring a subject in real time using a removable device worn on the subject, said method comprising:
    wirelessly capturing an acoustic signal using a sensor located within the removable device worn on the subject, the acoustic signal being indicative of breathing over a first period of time;
    inputting, at a processor located within the removable device worn on the subject, a first signal indicative of the captured acoustic signal from the sensor;
    removing, at the processor, noise from the first signal to create a second signal indicative of the breathing;
    computing, at the processor, a plurality of moving averages of the second signal using a temporal window defining a second period of time, wherein each moving average is an average value of the second signal across the temporal window;
    determining, at the processor, that at least one of the plurality of moving averages has a value of zero;
    identifying, at the processor, an apneic event in response to the determining; and
    reporting the identified apneic event using a visual display.

2. The method of claim 1, wherein the first signal has a first frequency and said method further comprises an act of down-sampling the first signal to a second lower frequency.

3. The method of claim 1, wherein the removing noise from the first signal comprises:
    estimating the noise over the first period of time; and
    subtracting the estimated noise from the first signal.

4. The method of claim 3, wherein the estimating the noise over the first period of time comprises filtering out portions of the first signal having an intensity less than twice a standard deviation of a distribution of signal intensity captured over the first period of time.

5. The method of claim 1, wherein the determining is indicative of no breathing during the temporal window that the at least one of the plurality of moving averages was computed.

6. The method of claim 1, further comprising counting a number of apneic events to determine a severity of apnea.

7. The method of claim 6, wherein the severity of the apnea comprises one of mild, moderate, or severe sleep apnea.

8. The method of claim 1, wherein the visual display comprises one or more indicators and the reporting comprises activating the one or more indicators based on the identified apneic event.

9. The method of claim 1, wherein the visual display is located on a second device, and said method further comprises:
    transmitting information associated with the identified apneic event to the second device via a transmitter.

10. A device for wirelessly monitoring a subject in real time, said device being configured to be worn on a body of the subject and comprising:
- an acoustic sensor for wirelessly capturing an acoustic breathing signal continuously over a first period of time;
- a visual display; and
- a processor in communication with said acoustic sensor and visual display, said processor adapted to:
  - input a first electrical breathing signal indicative of the captured acoustic signal from the acoustic sensor,
  - remove noise from the captured first electrical breathing signal to create a second breathing signal,
  - compute a plurality of moving averages of the second breathing signal using a temporal window defining a second period of time, wherein each moving average is an average value of the second breathing signal across the temporal window,
  - determine that the at least one of the plurality of moving averages has a value of zero,
  - identify an apneic event in response to the determining, and
  - report the identified apneic event using the visual display.

11. The device of claim 10, further comprising a second sensor for capturing a motion signal associated with a second condition of the subject.

12. The device of claim 10, wherein the visual display comprises at least one light emitting element and the processor reports the identified apneic event by illuminating the at least one light emitting element based on a status of the apneic event.

13. The device of claim 10, wherein the processor is configured to remove the noise from the first signal by:
- estimating the noise over the first period of time; and
- subtracting the estimated noise from the first signal.

14. The device of claim 13, wherein the estimating the noise over the first period of time comprises filtering out portions of the first signal having an intensity less than twice a standard deviation of signal intensity captured over the first period of time.

15. The device of claim 10, wherein the moving average having the value of zero is indicative of no breathing during the temporal window that the moving average was computed.

16. The device of claim 10, wherein the processor is configured to count a number of apneic events to determine a severity of apnea.

17. The device of claim 16, wherein the severity of the apnea comprises one of mild, moderate, or severe sleep apnea.

* * * * *